(12) United States Patent
Tass et al.

(10) Patent No.: US 8,538,547 B2
(45) Date of Patent: Sep. 17, 2013

(54) APPARATUS FOR THE STIMULATION OF NEURAL NETWORKS

(75) Inventors: Peter Tass, Munich (DE); Christian Hauptmann, Stolberg (DE)

(73) Assignee: Forschungszentrum Juelich GmbH, Juelich (DE)

( * ) Notice: Subject to any disclaimer, the term of this patent is extended or adjusted under 35 U.S.C. 154(b) by 522 days.

(21) Appl. No.: 12/739,426

(22) PCT Filed: Oct. 28, 2008

(86) PCT No.: PCT/DE2008/001746
§ 371 (c)(1),
(2), (4) Date: Apr. 29, 2010

(87) PCT Pub. No.: WO2009/056106
PCT Pub. Date: May 7, 2009

(65) Prior Publication Data
US 2010/0217355 A1 Aug. 26, 2010

(30) Foreign Application Priority Data
Oct. 30, 2007 (DE) .......................... 10 2007 051 848

(51) Int. Cl.
*A61N 1/36* (2006.01)
(52) U.S. Cl.
USPC .......................................................... 607/62

(58) Field of Classification Search
USPC .................................................... 607/42, 426
See application file for complete search history.

(56) References Cited

U.S. PATENT DOCUMENTS

| 6,529,774 | B1 | 3/2003 | Greene |
| 2003/0028072 | A1 | 2/2003 | Fischell |
| 2003/0045914 | A1* | 3/2003 | Cohen et al. .................... 607/62 |
| 2006/0095088 | A1 | 5/2006 | DeRidder |
| 2006/0212089 | A1 | 9/2006 | Tass |
| 2006/0224191 | A1 | 10/2006 | Dilorenzo |

FOREIGN PATENT DOCUMENTS

DE 10318071 A 11/2004

* cited by examiner

*Primary Examiner* — Niketa Patel
*Assistant Examiner* — Alyssa M Alter
(74) *Attorney, Agent, or Firm* — Andrew Wilford

(57) ABSTRACT

An apparatus (100) is described which comprises at least one measuring unit (31-34) for recording test signals from neurons, a generator unit (10) for generating electrical stimulation signals in accordance with the test signals, and a plurality of stimulation units (11-14) that are connected to the generator unit (10). The stimulation units (11-14) stimulate a plurality of neural networks in a deferred manner by means of the stimulation signals and thus induce a deferred activity in the stimulated neural networks.

16 Claims, 6 Drawing Sheets

APPARATUS FOR THE STIMULATION OF NEURAL NETWORKS

CROSS REFERENCE TO RELATED APPLICATIONS

This application is the US national stage of PCT application PCT/DE2008/001746, filed 28 Oct. 2008, published 7 May 2009 as WO2009/056106, and claiming the priority of German patent application 102007051848.1 itself filed 30 Oct. 2007.

FIELD OF THE INVENTION

The invention relates to an apparatus and a method for stimulating neural networks. In particular, the invention relates to an apparatus and a method for restoring the activity of central pattern generators.

Central pattern generators (CPG) are an important functional element of the central nervous system and are responsible for e.g. the control and initiation of movements. They are located in, for example, the spinal cord and in the brain stem. Central pattern generators are neural networks that endogenously, i.e. without external stimuli, generate rhythmically repeating patterns by the involved neurons "firing". The "firing" of a neuron denotes the generation of a short, electric pulse by means of which signals are transmitted to the neurons connected to the firing neuron.

A central pattern generator is composed of a plurality of neural networks, wherein the neurons within each neural network are active in a synchronized fashion, i.e. fire synchronously. The activity of the neural networks amongst themselves is shifted in time. Dysfunctions in the activity of central pattern generators can for example lead to severe motor disorders.

SUMMARY OF THE INVENTION

According to one refinement, an apparatus according to the invention comprises at least one measurement unit, a generator unit and a plurality of stimulation units coupled to the generator unit. Measurement signals of neurons are recorded by means of the measurement unit. The generator unit serves for generating electric stimulation signals, which are transmitted to the stimulation units. In the process, the stimulation signals are generated as a function of the measurement signals. The stimulation units in each case stimulate different neural networks using the stimulation signals. Furthermore, the stimulation units in each case apply the stimulation signals offset in time, e.g. each of the stimulation units starts the stimulation at a different time. The stimulation offset in time induces activity shifted in time into the stimulated neural networks.

As per a further refinement of the apparatus, stimulation signals can also be applied with different polarity, without or together with a time offset.

The apparatus can be used to restore the activity of central pattern generators.

Furthermore, the apparatus can be used for treatment after a stroke, in the case of "gait-ignition-disorder" disease or in the case of another motor disorder.

BRIEF DESCRIPTION OF THE DRAWING

The invention will be explained in more detail in the following text in an exemplary fashion, with reference being made to the drawings, in which.

DETAILED DESCRIPTION

Figure 1:
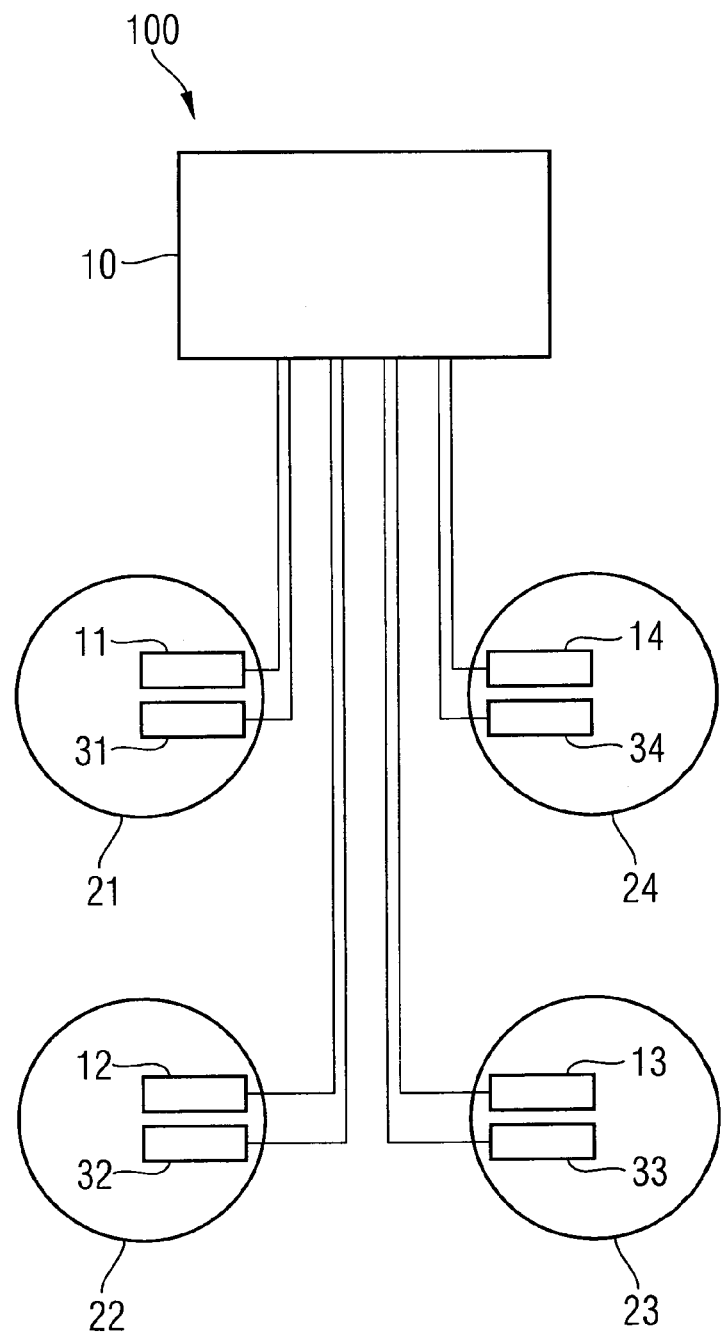
FIG. 1 shows a schematic illustration of an apparatus 100 as per an exemplary embodiment.

FIG. 1 schematically illustrates an apparatus 100. The apparatus 100 contains a generator unit 10 and a plurality of stimulation units 11, 12, 13 and 14, which are connected to the generator unit 10. In the present exemplary embodiment, there are four stimulation units; however, provision can also be made for two, three, five, six or more stimulation units.

Each of the stimulation units 11 to 14 is placed into the brain or into the region of the spinal cord of a human or animal such that the relevant stimulation unit stimulates a neural network 21, 22, 23 or 24, i.e. each stimulation unit 11 to 14 is associated with one of the neural networks 21 to 24. The neural networks 21 to 24 can be part of a central pattern generator.

During the operation of the apparatus 100, the generator unit 10 generates stimulation signals, which are fed into the stimulation units 11 to 14 and are used by the stimulation units 11 to 14 for stimulating the neural networks 21 to 24. In the process, the stimulation signals applied by different stimulation units 11 to 14 are in each case offset in time.

The neurostimulation that can be carried out with the aid of the apparatus 100 can induce rhythmic activity in each of the neural networks 21 to 24, wherein the rhythmic activities of different neural networks 21 to 24, or the phases thereof, are time-shifted with respect to one another. The time-shifted rhythmic activity of the neural networks 21 to 24 approximately corresponds to the normal, healthy activity of central pattern generators. In the process, the neurons within a neural network have the same activity, i.e. the neurons belonging to one and the same neural network fire synchronously. In the case of a suitable choice of stimulation locations, the stimulation by means of the apparatus 100 can be used in order to counteract the abnormal reduction in such rhythmic activity. This leads to a reduction in the pathological symptoms.

An abnormal reduction of the rhythmic activity of central pattern generators can be observed, for example, after a stroke or in "gait-ignition-disorder" disease or else in the case of Parkinson's disease. The apparatus 100 can be used for the treatment of such diseases.

The stimulation by means of the apparatus 100 can for example cause the neural networks 21 to 24 to assume the rhythm and the time offset prescribed by the stimulation, i.e. rhythm and time offset are stamped onto the stimulated neural networks by the stimulation signals. In the case of patients with dysfunctional central pattern generators, the stimulation can cause a long-lasting or even permanent stabilization of the healthy functionality of the neural networks.

In humans, central pattern generators are found, for example, in the region of the spinal cord. In addition to these, neural structures responsible for generating rhythmic activity are also located at other locations within the central nervous system, for example within the brain. By way of example, populations of so-called interneurons are found in the spinal cord, and these interneurons act as generators of coordinated movement activity. By way of example, such a central-pattern-generator structure can be realized by epidural stimulation at the dorsal surface of the spinal cord in the region of the lumbar spine. In the case of patients with a trauma of the spine, restoring the rhythmic activity by stimulating the central pattern generators in this region by means of the apparatus 100 can lead to initializing and carrying out the movement.

The same effect as in the time-offset application of the stimulation signals by the stimulation units 11 to 14 can be achieved if the stimulation signals are applied simultaneously but with different polarity. For example, if a sinusoidal signal is simultaneously applied at two stimulation locations and with different polarity, this corresponds to stimulation with a phase difference of 180°.

The apparatus 100 still additionally contains one or more measurement units 31 to 34, which record measurement signals from neurons, for example in the form of electric pulses, and transmit these signals to the generator unit 10. The generator unit 10 generates the stimulation signals as a function of the measurement signals. This mode of operation of the apparatus 100 is referred to as a "closed loop" mode.

By way of example, as shown in FIG. 1, one of the measurement units 31 to 34 can be placed into each of the target areas 21 to 24, and it measures the neuronal activity of the respective neural network 21 to 24, i.e. the firing by involved neurons, and transmits this information to the generator unit 10. Alternatively, the measurement units can be placed in only a part of the stimulated neural networks 21 to 24, or some or all measurement units can be arranged outside of the target areas 21 to 24. Hence, the physiological activity can be measured in one or more stimulated target areas and/or one or more areas connected thereto by means of the measurement units.

By way of example, the measurement units 31 to 34 can be designed as electrodes, in particular for measuring neuronal and/or vegetative activity, or as accelerometers. The number of measurement units is not limited. It is possible for only one measurement unit to be provided, but, as in the exemplary embodiment as per FIG. 1, a plurality of measurement units can also be implanted into the brain and/or into the region of the spinal cord.

Various refinements are feasible in respect of the interaction of the generator unit 10 with the measurement units 31 to 34. By way of example, the generator unit 10 can carry out a stimulation controlled by requirements. For this, the generator unit 10 detects the presence and/or the characteristic of one or more abnormal features on the basis of the measurement signals recorded by the measurement units 31 to 34. By way of example, the amplitude or the magnitude of the neuronal activity can be measured, and this can be used to determine whether the observed central pattern generator has a normal or pathological function. As soon as a certain reduction in the rhythmic activity of the central pattern generator is determined, the stimulation can be initiated. By way of example, for this, the rhythmic activity can be compared to one or more thresholds. In an alternative refinement, the phase difference in the neuronal activity can be used for the control by requirement. In this case, the phase differences in the neuronal activities of the individual populations of the central pattern generator, recorded by means of the measurement units 31 to 34, are determined and stimulation is activated when there is a deviation of the measured phase differences from predetermined values or the stimulation amplitude is matched to the deviation.

As an alternative to controlling the times of the stimulation on the basis of the measurement signals recorded by the measurement units 31 to 34 or in addition thereto, parameters of the stimulation signals can be set by the generator unit 10 on the basis of the characteristic of the abnormal features. By way of example, the generator unit 10 can set, on the basis of the measurement signals, the amplitude of the stimulation signals or the duration of the stimulation or the duration of stimulation pulse trains. Provided that the abnormal features determined on the basis of the recorded measurement signals reduce during the stimulation, the amplitude of the stimulation signals can be reduced in size and can finally tend to zero.

Moreover, provision can be made for the measurement signals recorded by the measurement units 31 to 34 to be used directly as stimulation signals, or possibly to be used after one or more processing steps, and to be fed into the stimulation units 11 to 14 by the generator unit 10. By way of example, the measurement signals can be amplified and be processed, if need be after mathematical calculation (e.g. after mixing of the measurement signals) with at least one time delay and linear and/or nonlinear calculation steps and combinations, and be fed into the stimulation units 11 to 14. By way of example, the calculation mode can be selected such that the abnormal reduction in the rhythmic activity is counteracted and the stimulation signal likewise disappears with reducing abnormal neuronal activity or at least is significantly reduced in its strength.

Figure 2:
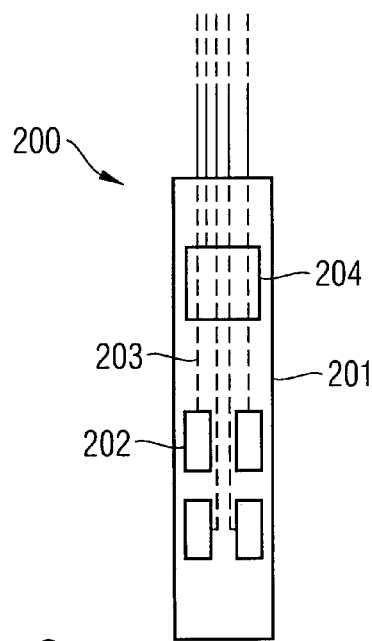
FIG. 2 shows a schematic illustration of a stimulation and measurement electrode 200.

FIG. 2 schematically illustrates an electrode 200, as can be used, for example, as a stimulation unit 11, 12, 13 or 14. The electrode 200 consists of an insulated electrode shaft 201 and at least one, for example two or more, stimulation contact surfaces 202, which have been introduced into the electrode shaft 201. The electrode shaft 201 and the stimulation contact surfaces 202 can be produced from a biocompatible material. Furthermore, the stimulation contact surfaces 202 are electrically conductive, by way of example they are made of a metal, and are in direct electrical contact with the nerve tissue after the implantation. In the present exemplary embodiment, each of the stimulation contact surfaces 202 can be actuated via its own input lead 203, or the recorded measurement signals can be conducted away via the input leads 203. As an alternative, two or more stimulation contact surface 202 can also be connected to the same input lead 203.

In addition to the stimulation contact surfaces 202, the electrode 200 can have a reference electrode 204, the surface of which can be greater than that of the stimulation contact surfaces 202. The reference electrode 204 is used during the stimulation of the nerve tissue in order to generate a reference potential.

As an alternative, it is also possible to use one of the stimulation contact surfaces 202 for this purpose.

In addition to its function as one of the stimulation units 11 to 14, the electrode 200 can also be used as one of the measurement units 31 to 34. In this case, measurement signals are recorded by at least one of the contact surfaces 202.

The contact surfaces 202 can be connected to the generator unit 10 via a cable or via telemetric connections.

Figure 3:
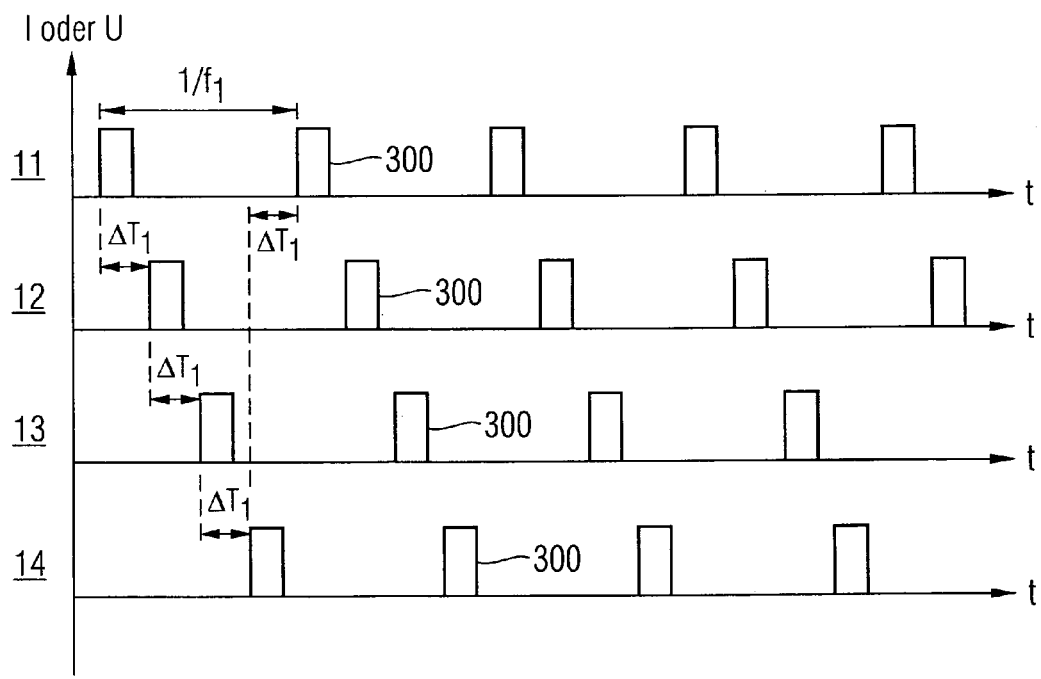
FIG. 3 shows a schematic illustration of sequences of stimulation signals 300 applied by means of a plurality of stimulation units.

A stimulation method that can for example be carried out by means of the apparatus 100, can be used when required and is suitable for restoring the normal functionality of central pattern generators is illustrated schematically in FIG. 3. FIG. 3 plots, one below the other, the stimulation signals 300 applied by the stimulation units 11 to 14 over time t.

By way of example, each of the stimulation units 11 to 14 periodically applies the stimulation signal 300 to the respective neural network 21 to 24. The frequency $f_1$, with which the stimulation signals 300 are repeated in each stimulation unit 11 to 14, can lie in the range of the natural rhythm with which the neurons of an individual neural network fire synchronously in the case of a healthy central pattern generator. By way of example, the frequency $f_1$ lies in the range from 0.05 to 20 Hz, in particular in the range from 0.05 to 10 Hz. Different types of movement can be characterized by different frequencies and, in particular, different phase differences of the individual neuron populations in the central pattern generator. The apparatus takes these differences into account by applying different programs for the corresponding movement patterns.

The application of the stimulation signals 300 via the individual stimulation units 11 to 14 is brought about with a time delay between the individual stimulation units 11 to 14. By way of example, the start of successive stimulation signals applied by different stimulation units can be shifted by a time $\Delta T_1$.

In the case of N stimulation units, the time delay $\Delta T_1$ between in each case two successive stimulation signals 300 can for example be in the region of one N-the of the mean period of the natural rhythm of an individual neural network. Since the mean frequency of the rhythmic activity in the case of healthy central pattern generators is approximately between 0.05 and 20 Hz, the time delay $\Delta T_1$ is for example in the region of 0.05 seconds/N to 20 seconds/N. In the most expedient case, this can achieve immediate control of the abnormal neuronal discharge patterns in the target region. Moreover, the stimulation can also achieve a long-term synaptic reorganization in the affected nerve cell networks, and so the target areas relearn the ability to form central-pattern-generator activity as a result of plastic procedures.

The time delay between two successive stimulation signals 300 does not necessarily always have to be the same size. Provision can by all means be made for the separations to be selected differently between the individual stimulation units 11 to 14. Additionally, the delay times can also be varied during the treatment of a patient. The delay times can also be adjusted in respect of the physiological signal run-times, in order to thereby take into account the physiological peculiarities of the stimulated central pattern generator.

As a result of the stimulation by means of the stimulation units 11 to 14, the rhythm that is prescribed by the stimulation and corresponds to the natural rhythm can be stamped onto the stimulated neural networks 21 to 24. After successful stimulation, the neurons within each of the neural networks 21 to 24 accordingly fire synchronously at a frequency substantially corresponding to the frequency $f_1$, or at a frequency deviating therefrom by up to ±10%. Additionally, the time offset of the activity of the individual neural networks 21 to 24 corresponds to the time offset $\Delta T_1$ with which the stimulation signals 300 were applied previously. It follows that after a successful stimulation, the pattern of the signals generated by the neural networks 21 to 24 corresponds to the stimulation pattern from FIG. 3.

It should be noted that in the case of the diseases described here, such as e.g. stroke, gait ignition disorder or other motor disorders, there is typically no abnormal complete synchronization of the neurons from a plurality of neural networks, i.e. the neurons of the neural networks 21 to 24 do not typically fire synchronously at one and the same time. Rather, prior to the stimulation, there is for example only a low correlation between the individual neural networks 21 to 24, and it is even possible that the neurons of the neural networks 21 to 24 may fire in an uncorrelated fashion before the stimulation.

Figure 4:
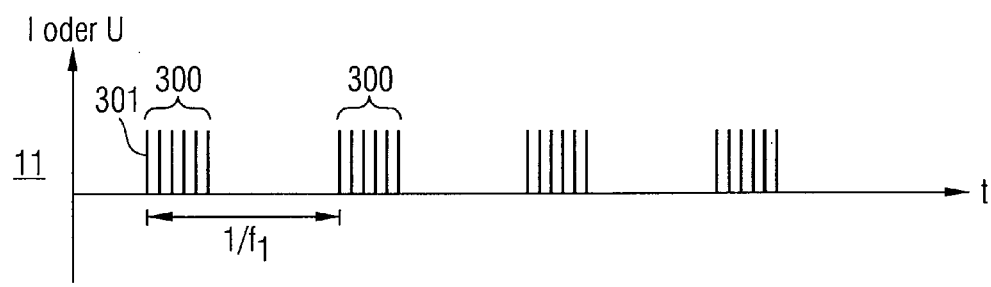
FIG. 4 shows a schematic illustration of a sequence of pulse trains 300 applied by means of a stimulation unit.

By way of example, current- or voltage-controlled pulses can be used as stimulation signals 300. Additionally, a stimulation signal 300 can be a pulse train consisting of a plurality of individual pulses 301, as is illustrated in FIG. 4 on the basis of the example of the stimulation unit 11. The pulse trains 300 can each consist of between 1 and 100, in particular between 2 and 10, electric charge-balanced individual pulses 301. The pulse trains 300 are applied, for example, as a sequence of up to 20 or even more pulse trains 300. Within one sequence, the pulse trains 300 are repeated at the frequency $f_1$ in the region of 0.05 to 20 Hz.

By way of example, the amplitude of the individual pulses 301 can be set on the basis of the measurement signals recorded by means of the measurement units 31 to 34. Provided that the rhythmic firing of the examined neural networks is present only weakly or not at all, a larger amplitude is selected for the individual pulses 301. As soon as the behavior of the neural networks approaches the normal, healthy behavior of a central pattern generator more closely, the amplitude of the individual pulses 301 can be reduced.

Figure 5:
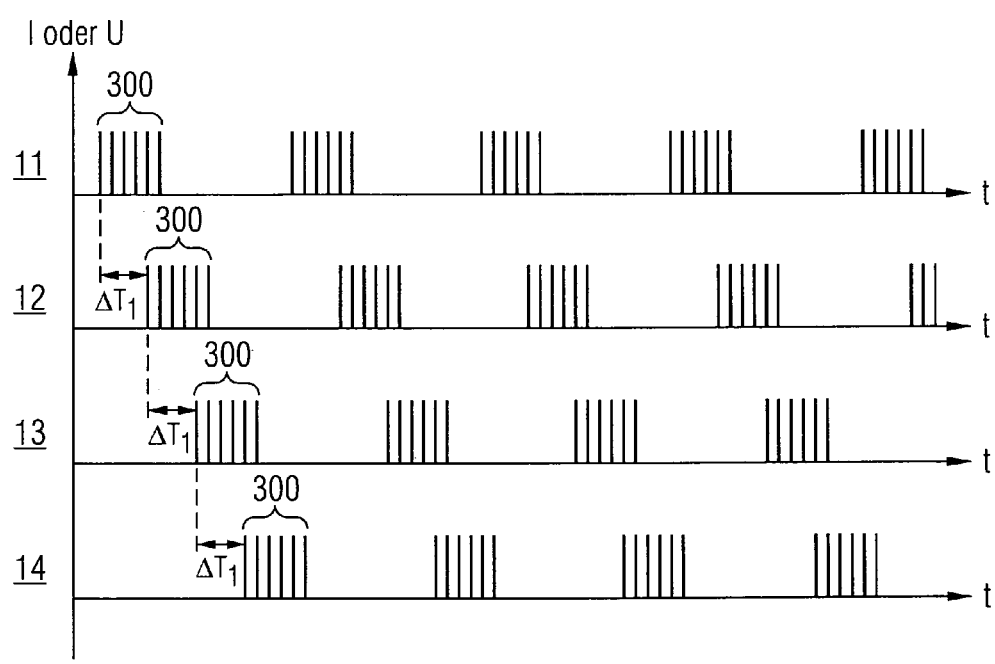
FIG. 5 shows a schematic illustration of sequences of pulse trains 300 applied by means of a plurality of stimulation units.

FIG. 5 once again illustrates the stimulation method already shown in FIG. 3 with the pulse trains 300 as stimulation signals.

Figure 6:
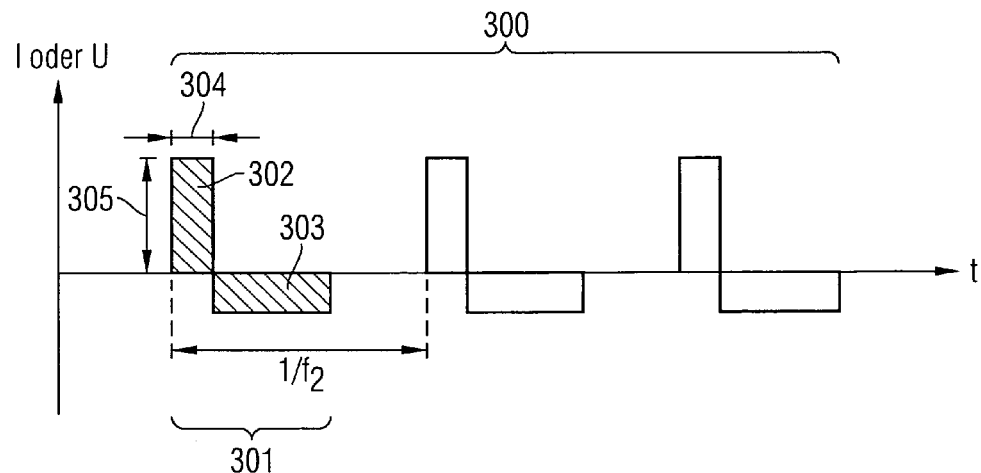
FIG. 6 shows a schematic illustration of a pulse train 300.

FIG. 6 shows, in an exemplary fashion, a pulse train 300, which consists of three individual pulses 301. The individual pulses 301 are repeated at a frequency $f_2$ of between 50 and 250 Hz, in particular above 100 Hz. The individual pulses 301 can be current- or voltage-controlled pulses, which comprise an initial pulse component 302 and a pulse component 303 flowing in the opposite direction and following the former, wherein the polarity of the two pulse components 302 and 303 can also be interchanged in relation to the polarity shown in FIG. 6. The duration 304 of the pulse component 302 lies in the region of between 1 µs and 450 µs. In the case of current-controlled pulses, the amplitude 305 of the pulse component 302 lies in the region between 0 mA and 25 mA, and in the case of voltage-controlled pulses, the amplitude is in the region of between 0 and 16 V. The amplitude of the pulse component 303 is smaller than the amplitude 305 of the pulse component 302. In return, the duration of the pulse component 303 is longer than that of the pulse component 302. The pulse components 302 and 303 are ideally dimensioned such that the charge transferred by them is the same in both pulse components 302 and 303, i.e. the areas shaded in FIG. 6 are of the same size. As a result of this, an individual pulse 301 introduces the same amount of charge into the tissue as is taken from the tissue.

The rectangular shape of the individual pulses 301 illustrated in FIG. 6 represents an ideal shape. There is a deviation from the ideal rectangular shape depending on the quality of the electronics generating the individual pulses 301.

Instead of pulse-shaped stimulation signals, the generator unit 10 can for example also generate differently shaped stimulation signals, e.g. temporally continuous stimulus patterns. The above-described signal shapes and the parameters thereof should only be understood as being exemplary. Provision can by all means be made for there to be deviation from the aforementioned signal shapes and the parameters thereof. Additionally, it is feasible for the stimulation to be brought about by the patient, for example by means of telemetric activation. In this case, the patient can activate the stimulation for a predetermined period of e.g. 5 minutes, for example by means of an external transmitter, or the patient can independently start and stop the stimulation.

Figure 7:
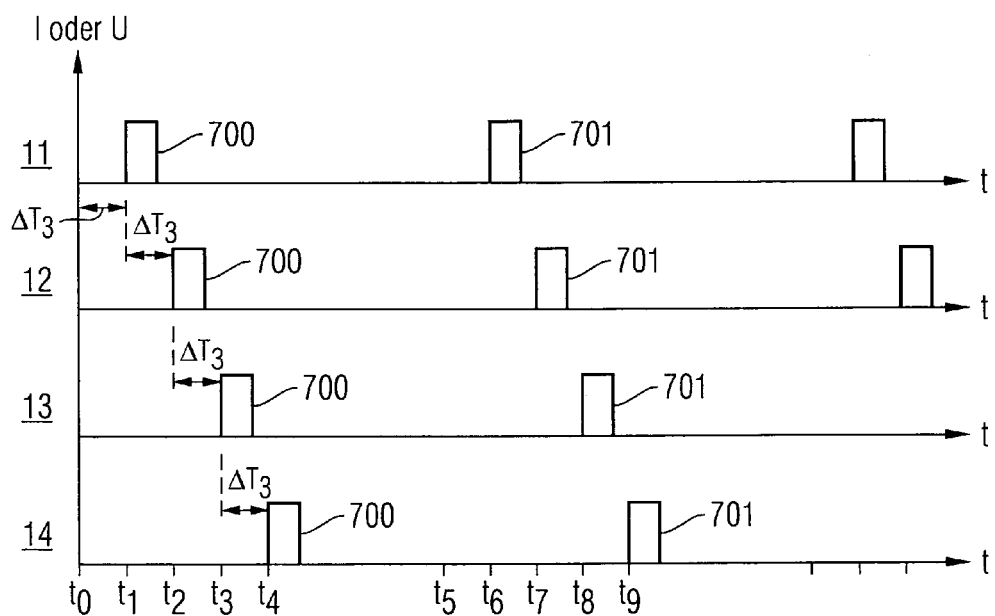
FIG. 7 shows a schematic illustration of stimulation signals 700 and 701 applied by means of a plurality of stimulation units and obtained from measurement signals.

FIG. 7 illustrates, in an exemplary and schematic fashion, a stimulation method suitable for restoring the normal functionality of central pattern generators, which method is based on a measurement signal being recorded by means of one or more measurement units 31 to 34 and this measurement signal being used as a stimulation signal for stimulating the neural networks, either directly, i.e. without further processing steps, or after one or more processing steps. FIG. 7 plots, one below the other, the stimulation signals applied by the stimulation units 11 to 14 over time t.

In the present stimulation, one or more measurement signals are recorded at a time t0 by means of at least one of the measurement units 31 to 34. The measurement signals can subsequently be used directly as stimulation signal 700 or are first of all subjected to processing, for example linear processing such as e.g. amplification, and are subsequently fed into the stimulation units 11 to 14 as stimulation signals 700. Provided that more than one measurement signal is recorded, the measurement signals can also be interconnected.

As per one refinement, the stimulation signal 700 is based on a pulse train, like, for example, the pulse train 300 shown in FIG. 4, the amplitude of which is modulated by the measurement signal and thereafter fed into the stimulation units 11 to 14.

The stimulation signal 700 is fed into the various stimulation units 11 to 14 with a time delay. In FIG. 7, the start times of the respective stimulations are denoted by $t_1$ to $t_4$. There is a delay of a time interval $\Delta T_3$ between the times $t_1$ to $t_4$ and the respectively preceding time t0 to t3. The time interval $\Delta T_3$ can be selected analogously to the time interval $\Delta T_1$ described in conjunction with FIG. 3, i.e. delay times in the region of between 0.05 second/N and 20 seconds/N can be selected, with N specifying the number of stimulation units.

After the stimulation by means of the stimulation signal 300, there can be a renewed stimulation. For this, the next measurement signal can for example already be recorded at the time $t_4$, but it can also, as illustrated in FIG. 7, only be recorded at a later time $t_5$. The measurement data determined at the time $t_5$ generates a new stimulation signal 701, which is fed into the stimulation units 11 to 14 at the times $t_6$ to $t_9$. The interval between the times $t_5$ to $t_9$ is again $\Delta T_3$ in each case.

The stimulation can be continued accordingly. The stimulation can either be terminated or interrupted after a certain number of cycles, or the measurement signals can be used to check whether a sufficiently rhythmic activity of the neural networks was obtained by means of the stimulation and accordingly the stimulation can be continued or terminated. Like in the stimulation shown in FIGS. 3 and 5, the stimulation as per FIG. 7 should also stamp the rhythm onto the stimulated neural networks 21 to 24, which rhythm is prescribed by the stimulation and corresponds to the natural rhythm.

According to one refinement, the interval between two successive stimulation signals is not always $\Delta T_3$, but the intervals are selected differently between the individual stimulation units 11 to 14 and/or are adjusted during the treatment of the patient. This makes it possible to take into account, for example, physiological signal run-times of the stimulated central pattern generators.

A further alternative to the stimulation method described above can consist of not recording the measurement signals at a single time, but recording them over a time interval. This time interval can for example correspond to the duration of the period of the normal rhythmic activity. By way of example, it is possible to form the variance from the signals recorded during this time interval and this variance can be used as a stimulation signal, either directly or after further processing.

As already described further above, the interval between two successive stimulations by means of the same stimulation unit can in principle be selected freely. By way of example, the time period $N \times \Delta T_3$ or an integer multiple thereof can be selected as the interval, such that the stimulation signals always stimulate the stimulated neural network with the same phase.

Figure 8:
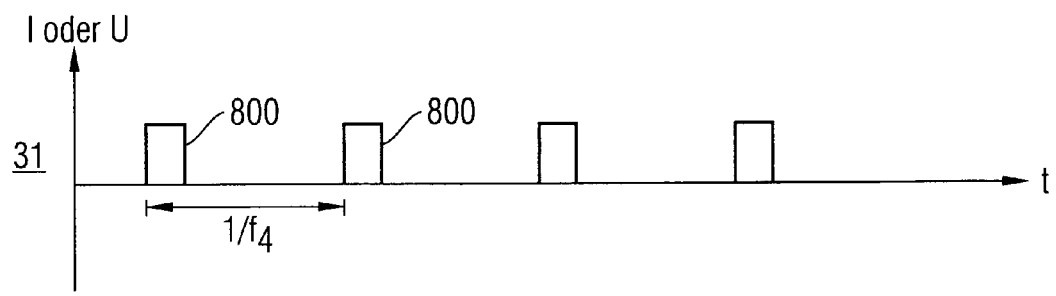
FIG. 8 shows a schematic illustration of measurement signals 800 recorded by means of a measurement unit.

Further types of stimulation are explained in the following text on the basis of FIGS. 8 and 9. In FIG. 8, measurement signals 800 are plotted over time t. By way of example, the measurement signals 800 are recorded by means of the measurement unit 31, which was implanted into the neural network 21. FIG. 8 shows that the neurons of the neural network 21 for example generate electric signals with a certain periodicity. The measurement signals 800 can have the form of bursts, within which the signals generated by the involved neurons are arranged. The bursts 800 are repeated at a frequency $f_4$ in the region of 0.05 to 20 Hz.

The measurement signals 800 either can be fed into the stimulation units 11 to 14 in an unchanged form, or they can be firstly subjected to processing steps and thereafter be used as stimulation signals. By way of example, the measurement signals 800 can be filtered by means of a bandpass or low pass filter and possibly be amplified before they are used as stimulation signals. Furthermore, the measurement signals 800 can be fed into the individual stimulation units 11 to 14 with a delay. Such a type of stimulation is illustrated schematically in FIG. 9. What is shown there is that stimulation signals 900, obtained from the measurement signals 800, are fed into the stimulation units 11 to 14 with a time offset.

The stimulation signals 900 can for example be generated by filtering the measurement signals 800 by means of a bandpass or low pass filter and modulating the amplitude of short pulse trains, like e.g. the pulse trains 300 illustrated in FIG. 4, by means of the signals obtained therefrom. This results in the stimulation signals 900 having the same period length $1/f_4$ as the measurement signals 800. The stimulation signals 800 can be fed into the stimulation unit 11 with the same phase as the measurement signals 800, which stimulation unit is implanted into the neural network 21 just like the measurement unit 31. This can result in the stimulation signals 900 stabilizing the natural rhythm of the neural network 21, which stimulation signals are applied simultaneously with the bursts 800 generated by the neurons.

Figure 9:
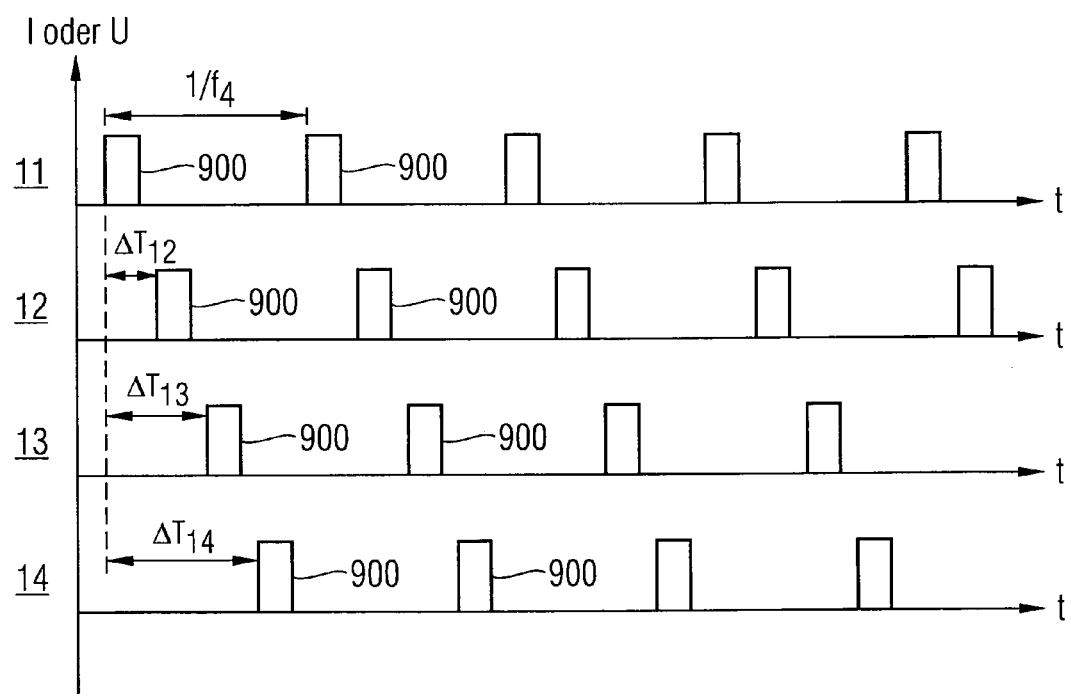
FIG. 9 shows a schematic illustration of stimulation signals 900 applied by means of a plurality of stimulation units and obtained from measurement signals.

Moreover, the stimulation signals 900 can be applied to the neural networks 22 to 24 via the stimulation units 12 to 14 with the delays $\Delta T_{12}$, $\Delta T_{13}$ or $\Delta T_{14}$ shown in FIG. 9. This can stabilize the natural rhythm of the neural networks 22 to 24 or the former can be induced into these neural networks, provided that the relevant neural networks do not have a rhythm or have an abnormal rhythm prior to stimulation.

The delays $\Delta T_{12}$, $\Delta T_{13}$ and $\Delta T_{14}$ either can be selected freely as described above or they can be determined by measurements. By way of example, an excitation signal, e.g. a pulse-shaped signal, can be applied by the stimulation unit 11. Thereafter, response signals are recorded by means of the measurement units 32 to 34 and the times respectively passing between the excitation signal and the response signals are used as the delay times $\Delta T_{12}$, $\Delta T_{13}$ and $\Delta T_{14}$ for the respective stimulation unit 12 to 14. As a result, this type of stimulation can induce rhythmic activity into the neural networks 21 to 24, which mirrors the stimulation pattern, as shown in FIG. 9, or at least is very similar thereto and which corresponds to the normal, healthy rhythmic activity of the stimulated central pattern generator.

Figure 10:
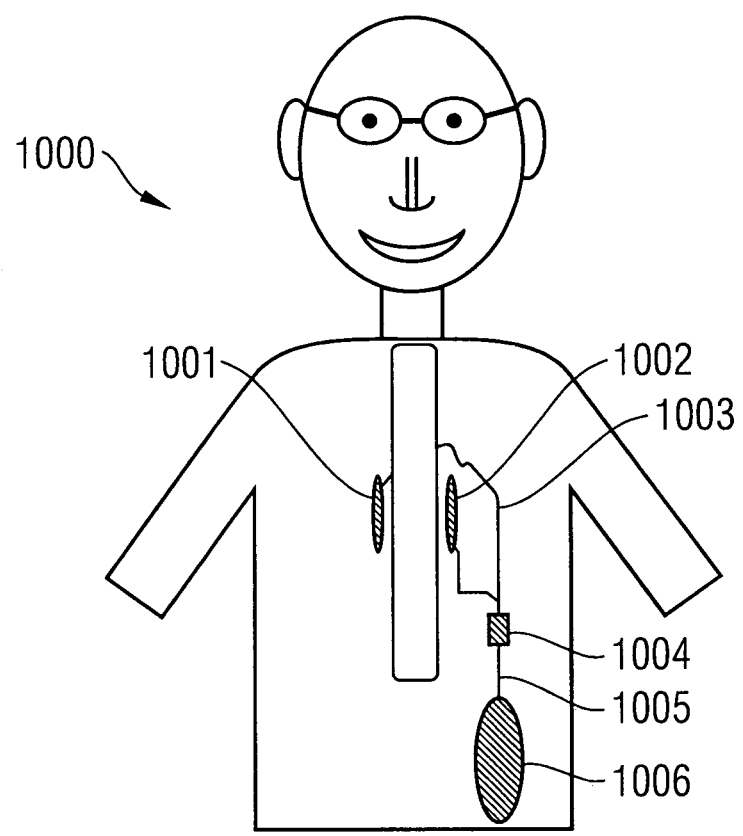
FIG. 10 shows a schematic illustration of an apparatus 1000 as per a further exemplary embodiment.

FIG. 10 illustrates an apparatus 1000 for restoring the normal functionality of central pattern generators by means of stimulation of neurons during the intended operation thereof. For this, stimulation electrodes 1001 and 1002 have been implanted in the region of the spinal cord of a patient. Each of the stimulation electrodes 1001 and 1002 is connected to a different neural network belonging to the same central pattern generator. Furthermore, the apparatus 1000 has at least one sensor, which, for example, is integrated into the stimulation electrodes 1001 and/or 1002. The stimulation electrodes 1001 and 1002 are each connected with an electrode cable 1003 to a generator unit 1006 via a connector 1004 and a connection cable 1005. All parts of the apparatus 1000 are implanted in the body of the patient. The generator unit 1006 can contain control electronics that realize the stimulation methods. The generator unit 1006 can comprise a long-life battery or a rechargeable accumulator as a source of energy. By way of example, the generator unit 1006 can be placed subcutaneously in the region of the lower abdomen of the patient. In an alternative refinement, the generator unit 1006 can be a semi-implant with an energy source located outside of the body. The generator unit 1006 can then have a safety switch that ensures that safety limits, such as e.g. a maximum acceptable charge intake, known to a person skilled in the art, are maintained.

The invention claimed is:

1. An apparatus comprising:
   at least one measurement unit for recording measurement signals of neurons,
   a generator unit for generating electric stimulation signals as a function of the measurement signals, and
   a plurality of stimulation units connected to the generator unit, wherein the stimulation units stimulate a plurality of neural networks with the stimulation signals offset in time and at a frequency $f_1$, and thereby induce activity shifted in time in the stimulated neural networks, wherein the stimulation signals are sequences of pulse trains and the pulse trains are modulated by a modulation signal obtained from the measurement signals, the number of stimulation units being N and the delay between the stimulation signals applied by the stimulation units substantially corresponding to a term of $1/(f_1 \times N)$.

2. The apparatus defined in claim 1, wherein the generator unit makes a decision as a function of the measurement signals as to whether stimulation is carried out by means of the stimulation units.

3. The apparatus defined in claim 1, wherein the generator unit determines one parameter of the stimulation signals, in particular the strength of the stimulation signals, as a function of the measurement signals.

4. The apparatus defined in claim 1, wherein the generator unit generates the stimulation signals as a function of a comparison between the measurement signals and one or more predetermined thresholds.

5. The apparatus defined in claim 1, wherein the frequency $f_1$ corresponds to a frequency at which a neural network of a healthy central pattern generator generates electric signals.

6. The apparatus defined in claim 1, wherein the stimulated neural networks are part of a central pattern generator.

7. Use of the apparatus defined in claim 1 for restoring the activity of a central pattern generator.

8. The use of the apparatus defined in claims 7 for treatment after a stroke or in the case of a gait-ignition-disorder disease or in the case of Parkinson's disease or in the case of another motor disorder or in the case of a spinal trauma.

9. A method comprising the steps of:
   recording measurement signals of neurons,
   generating electric stimulation signals as a function of the measurement signals and with a frequency $f_1$, and
   stimulating a plurality of neural networks offset in time by the stimulation signals and this induces activity shifted in time in the stimulated neural networks, wherein the stimulation signals are sequences of pulse trains and the pulse trains are modulated before the stimulation by a modulation signal obtained from the measurement signals, the number of stimulated neural networks being N and the delay between the stimulation signals applied to different neural networks substantially corresponding to a term of $1/(f_1 \times N)$.

10. The method defined in claim 9, wherein a decision is made as a function of the measurement signals as to whether stimulation is carried out.

11. The method defined in claim 9, wherein a parameter of the stimulation signals, in particular the strength of the stimulation signals, is determined as a function of the measurement signals.

12. The method defined in claim 9, wherein the stimulation signals are generated as a function of a comparison of the measurement signals and one or more predetermined thresholds.

13. The method defined in claim 9, wherein the frequency $f_1$ corresponds to a frequency at which a neural network of a healthy central pattern generator generates electric signals.

14. The method defined in claim 9, wherein the stimulated neural networks are part of a central pattern generator.

15. The method defined in claim 9, wherein the method is used to restore the activity of a central pattern generator.

16. The method defined in claim 9, wherein the method is used for treatment after a stroke or in the case of a gait-ignition-disorder disease or in the case of Parkinson's disease or in the case of another motor disorder or in the case of a spinal trauma.

* * * * *